(12) United States Patent
Auten et al.

(10) Patent No.: US 6,217,171 B1
(45) Date of Patent: *Apr. 17, 2001

(54) COMPOSITE OPHTHAMIC LENS

(75) Inventors: Richard Dale Auten, Cumming; John Lally, Loganville; Xiao-Xiao Zhang, Suwanee, all of GA (US)

(73) Assignee: Novartis AG, Basel (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/084,656

(22) Filed: May 26, 1998

(51) Int. Cl.$^7$ ....................................... G02C 7/04
(52) U.S. Cl. .................. 351/160 H; 351/160 R; 351/161
(58) Field of Search .................. 351/159, 160 H, 351/160 R, 161, 162, 177

(56) References Cited

U.S. PATENT DOCUMENTS

| | | | |
|---|---|---|---|
| 2,597,055 | 5/1952 | Baudry et al. | |
| 3,488,111 | 1/1970 | Isen | 351/160 |
| 3,489,491 | 1/1970 | Creighton | 351/160 |
| 3,560,598 | 2/1971 | Neefe | 264/1 |
| 3,619,044 | 11/1971 | Pandurang | 351/160 |
| 3,684,357 | 8/1972 | Tseutaki | 351/161 |
| 3,726,587 | 4/1973 | Kendall | 351/161 |
| 3,876,581 | 4/1975 | Neogi | 260/29.7 |
| 3,915,609 | 10/1975 | Robinson | 425/174.6 |
| 3,944,347 | 3/1976 | Barkdoll | 351/160 |
| 3,973,838 | 8/1976 | Page | 351/160 |
| 3,984,506 | 10/1976 | Tsuetaki | 264/1 |
| 4,208,362 | 6/1980 | Deichert et al. | 264/1 |
| 4,302,081 | 11/1981 | Tsuetaki | 351/161 |
| 4,666,249 | 5/1987 | Bauman et al. | 351/160 |
| 4,701,288 | 10/1987 | Cook et al. | 264/1.4 |
| 4,702,574 | 10/1987 | Bawa | 351/162 |
| 4,921,205 | 5/1990 | Drew et al. | 249/61 |
| 4,981,342 | 1/1991 | Fiala | 350/403 |
| 5,018,849 | 5/1991 | Su | 351/162 |
| 5,073,021 | * 12/1991 | Marron | 351/168 |
| 5,433,746 | 7/1995 | Namdaran | 623/6 |
| 5,433,898 | 7/1995 | Thakar | 264/1.7 |
| 5,508,317 | 4/1996 | Mueller | 522/85 |
| 5,712,721 | * 1/1998 | Large | 351/168 |

FOREIGN PATENT DOCUMENTS

| | | |
|---|---|---|
| 0378512A2 | 7/1990 | (EP) . |
| 0492126 | 7/1992 | (EP) . |
| 0574352A1 | 2/1993 | (EP) . |
| 2208775 | 12/1973 | (FR) . |
| 1412439 | 12/1974 | (GB) . |
| WO9406485 | 3/1994 | (WO) . |
| WO9406621 | 3/1994 | (WO) . |
| WO9623648 | 8/1996 | (WO) . |
| WO9710527 | 9/1996 | (WO) . |

* cited by examiner

Primary Examiner—Scott J. Sugarman
(74) Attorney, Agent, or Firm—R. Scott Meece; Robert J. Gorman, Jr.

(57) ABSTRACT

The invention provides a molded ophthalmic lens having at least first and second optical components, wherein the first optical component is cast molded to encapsulate the second optical component such that the first optical component provides an optical function and the second optical component provides an additional optical function. The invention additionally provides a process for producing a molded composite ophthalmic lens.

10 Claims, 2 Drawing Sheets ic devices.
COMPOSITE OPHTHAMIC LENS

BACKGROUND OF THE INVENTION

The present invention relates to ophthalmic devices. More particularly the invention is directed to composite ophthalmic devices.

The use of various ophthalmic devices, such as contact lenses and corneal implants, are known for the correction of vision abnormalities. Such ophthalmic devices typically are designed to correct one abnormality, e.g., myopia, and made from one optical polymeric material. There have been attempts to produce composite contact lenses having more than one polymeric material. Composite contact lenses having a relatively hard center section circumscribed by a soft and wettable edge section have been disclosed by various publications. The soft and wettable edge section of the lens is designed to provide improved comfort on the eye, thereby reducing the eye irritation often experienced by hard contact lens users. Additionally, there have been attempts to produce bifocal rigid contact lenses having two optical materials having different indices of refraction. Such attempts typically produce a composite lens by laminating or cementing two separately produced, e.g. lathe formed, component lenses. However, the cementing approach requires perfectly or near perfectly matching component lenses to produce the composite lens. In addition, the process for separately producing component lenses and the process for precisely cementing the component lenses are labor intensive and time consuming and are not conducive to mass producing bifocal lenses. Moreover, the cementing process is not highly suitable for producing hydrogel contact lenses since typical hydrogel contact lenses are formed in a dehydrated state and subsequently hydrated. When a hydrogel lens is hydrated, the lens swells and changes its dimension. Consequently, a composite hydrogel lens additionally experiences optical distortion and delamination problems.

There remains a need for composite lenses that can be produce with a production process that is simple and can easily be used to mass produce such lenses.

SUMMARY OF THE INVENTION

There is provided in accordance with the present invention a molded ophthalmic lens having a first optical component and a second optical component, wherein the first optical component is cast molded to encapsulate the second optical component such that the first optical component provides an optical function and the second optical component provides an additional optical function. The term "optical function" is used hereinafter to indicate both optical and ophthalmic functions, unless otherwise indicated. Desirably, the first optical material is a polymerizable or crosslinkable material that does not significantly shrink while being cured. More desirably, the first optical material is a polymerizable or crosslinkable material that does not significantly shrink or expand while being cured and processed thereafter.

The invention additionally provides a process for producing a molded composite ophthalmic lens. The process has the steps of providing a pre-lens, which is formed from a first optical material, wherein the pre-lens is a cured product of a curable first optical material and the pre-lens has an upper surface and a lower surface; providing a second optical material on the upper surface; placing an amount of the first optical material such that the second optical material is encapsulated by the pre-lens and the first optical material; and curing the first optical material encapsulating the second optical material in a finishing mold assembly, thereby affixing the second optical material and cast molding the ophthalmic lens.

The composite ophthalmic lens of the present invention is highly suitable for providing more than one optical and/or ophthalmic functions. Unlike prior art composite lenses, the ophthalmic lens can be produced conveniently using an insert molding process, which is a modified cast molding or double side molding process. The present molding process provides a fully formed composite lens, and therefore, the molded lens does not require additional handling and can be mass produced. In addition, the molding process is particularly suitable for producing soft hydrogel composite lenses having more than one optical or ophthalmic functions.

DETAILED DESCRIPTION OF THE INVENTION

Figure 1:
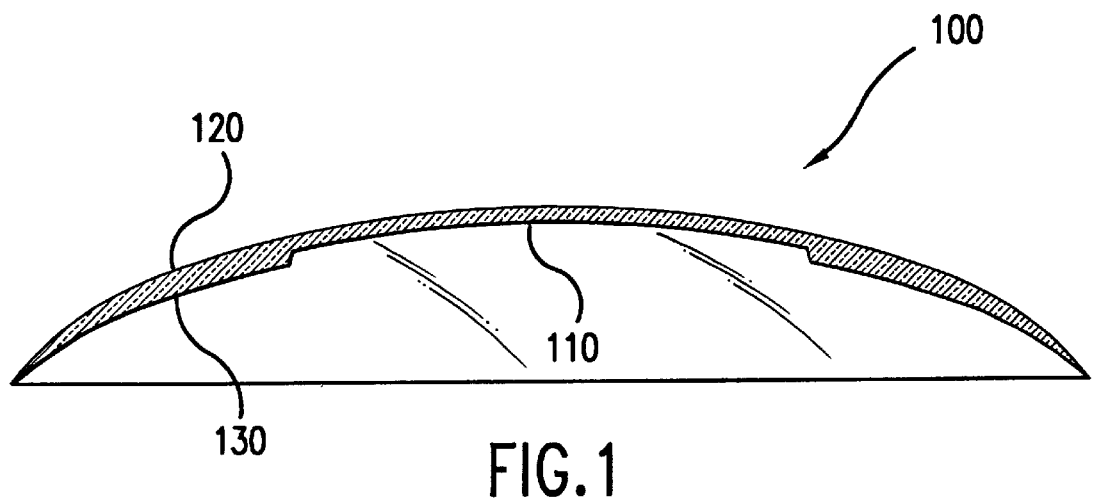
FIG. 1 is a cross section of the pre-lens formed from the first optical material.
Figure 2:
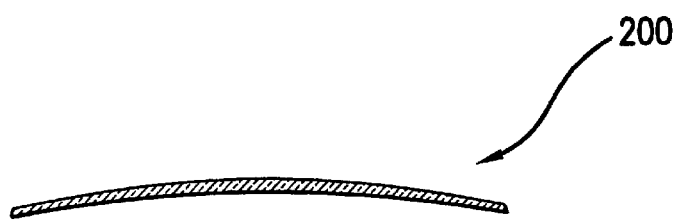
FIG. 2 is a cross section of the second optical material layer.
Figure 3:
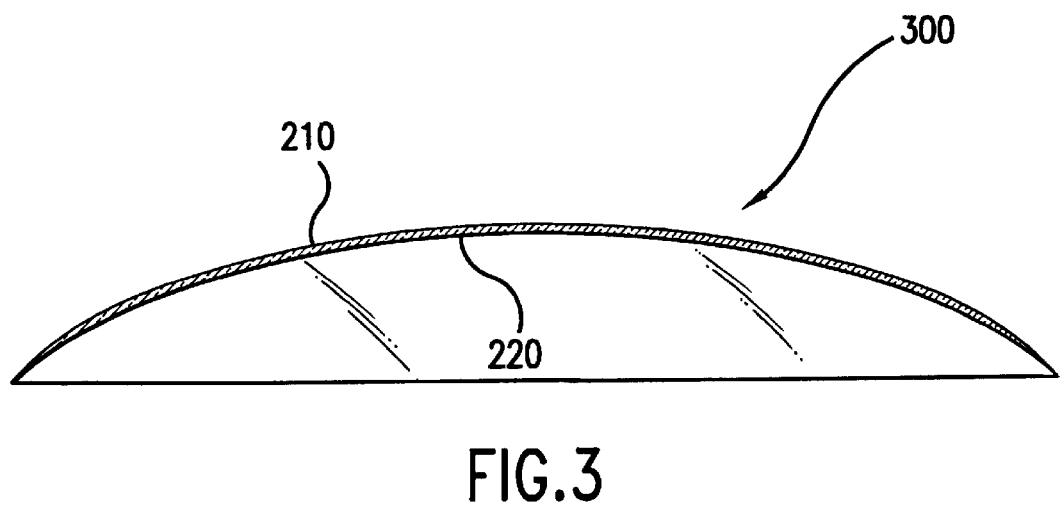
FIG. 3 is a cross section of the back surface of first optical material.
Figure 4:
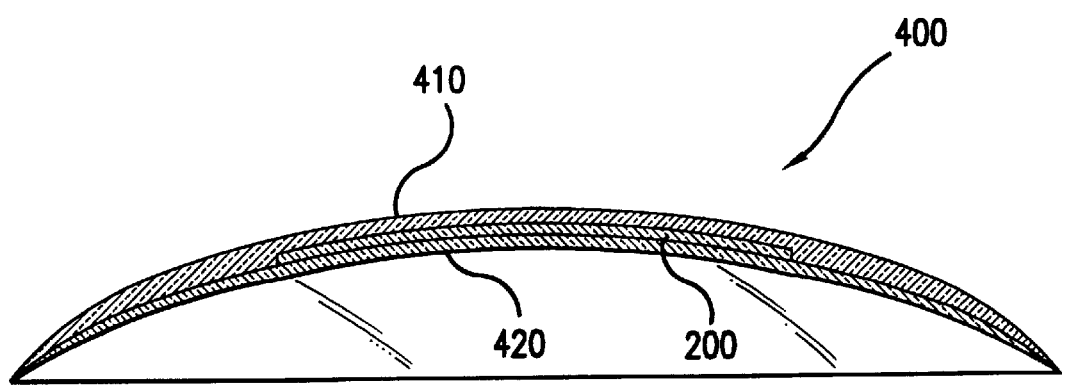
FIG. 4 is a cross section of the ophthalmic lens of the present invention containing the second optical material encapsulated within the first optical material.

The present invention provides a molded multifunctional composite ophthalmic lens that provides at least two optical functions. The ophthalmic lens of the present invention contains at least two optical materials, i.e., first and second optical materials. In accordance with the invention, the first optical material encapsulates the second optical material such that the second optical material is stably affixed or embedded in the first optical material. It is to be noted that the present multifunctional ophthalmic lens is described with a lens having two optical components for illustration purposes only, and the ophthalmic lens may contain more than two optical components. The term "ophthalmic lens" as used herein indicates a lens that is placed on or in the eye, and such ophthalmic lenses include contact lenses, corneal implants, corneal onlays and intraocular lenses. An ophthalmic lens (400) typically has an outer convex surface (410) and an inner concave surface (420), and the two curved surfaces are relatively flat, which curved surfaces are hereinafter referred to as "flat curves".

The multifunctional ophthalmic lens can be designed to provide combinations of many useful ophthalmic and optical functions. Such functions useful for the present invention include refractive functions, diffractive functions, birefringent functions, protective functions, cosmetic functions (e.g., iris color alteration), light filtration, polarization and the like. For example, a first component having one refractive power similar to a conventional contact lens and a second component having a different refractive or diffractive power can be used to create a bifocal composite ophthalmic lens of the present invention. Similarly, a light filtering ophthalmic lens can be produced by embedding an optical filter material in a first optical lens material.

In accordance with the present invention, the multifunctional ophthalmic lens can be produced by an insert molding process in which a first optical material is molded to encapsulate or embed a second optical material. An exemplary insert molding process has the steps of: first, a pre-lens (100) is formed in a pre-lens mold assembly, which has a matching set of a male mold half and a female mold half, from a first optical material; second, a second optical material layer (200) is formed or placed on one of the flat curves (130) of the pre-lens; and then an additional first optical material layer (300) is formed over the second optical material layer (300) and the previously polymerized first optical material layer (100), encapsulating and affixing the second optical material within the first optical material.

More desirably, the first step can be conducted by placing a fluid first optical material in the female pre-lens mold half of a pre-lens mold assembly, placing the male pre-lens mold half over the female pre-lens mold half to define the shape of the pre-lens, and then curing the optical material to form a pre-lens (100). In accordance with the present invention, the male and female pre-lens mold halves are assembled to form a pre-lens cavity that defines the shape of the pre-lens and is thinner or thinner and smaller than the final multifunctional ophthalmic lens. Accordingly, the pre-lens (100) produced from the pre-lens mold assembly is thinner or thinner and smaller than the final lens (400). Lens mold assemblies suitable for the pre-lens are conventional lens molds, provided that the mold assemblies are modified to form a thinner or thinner and smaller lens cavity than the size of the final multifunctional ophthalmic lens. For example, U.S. Pat. Nos. 4,865,779 to Ihn et al.; 5,271,875 to Appleton et al. and 5,238,388 to Tsai. disclose examples of suitable lens mold assemblies.

As another embodiment of the invention, one of the pre-lens mold halves may have a protruded region, e.g., at the center of the optical zone of the pre-lens, such that the pre-lens (100) produced from the mold assembly has an indented area or a pocket (110). The indented area (110) of the pre-lens provides a convenient and useful area to which the second optical material of the present invention can be placed to form the second optical material layer (200).

According to one preferred embodiment of the present invention, one flat curve of the pre-lens (120) is the functional optical surface of the final multifunctional ophthalmic lens, i.e., the front optical curve (410) or the back optical curve, (420) such that no additional step is required to finish the front or back optical curve, respectively. In this embodiment, the opposite flat curve of the functional optical surface of the pre-lens is a transitory surface (130) that receives a second optical material (200). Hereinafter this preferred embodiment is referred to as the "finished curve" embodiment.

Once the pre-lens mold assembly is filled and closed, while applying a holding pressure to stably close the mold assembly and maintain the shape of the pre-lens cavity, the first optical material in the mold assembly is polymerized or crosslinked to form a pre-lens having the contour of the pre-lens mold cavity. Hereinafter, for illustration purposes, the term "cured" is used to indicate that a polymerizable or crosslinkable fluid material is polymerized or crosslinked to form a solid or semi-solid material, unless otherwise indicated. When the optical material is cured, the mold assembly is opened to expose at least one flat curve of the pre-lens. As stated above, it is a preferred embodiment of the present invention that one of the cavity-forming surfaces of the pre-lens mold assembly forms the front or back optical curve of the final multifuictional lens. When the finished curve embodiment of the present invention is practiced, it is desirable to open the mold assembly in such a way that the front or back optical curve (120, 220) remains adhered to the mold surface, exposing only the transitory surface of the pre-lens (130, 210). For example, when a pre-lens is produced in a pre-lens mold assembly that has the front optical curve (410) of the final lens, (400) it is highly desirable to have the front curve side (120) of the pre-lens remain adhered to the female mold when the mold assembly is opened. Any known lens mold opening method or lens mold design that ensures selective adherence of the molded lens to one mold half can be employed. For example, the male and female mold halves of the pre-lens mold assembly can be produced from polymers having different surface energy properties such that the cured pre-lens adheres more firmly to the desired mold half of the pre-lens mold assembly. Alternatively, the polymer for or the surface of one mold half of the mold assembly can be modified, e.g., chemically or electromagnetically, to alter the surface energy properties of the polymer. For example, the optical surface of a mold half can be corona treated to modify the surface properties. Yet another known method uses a thermal gradient to ensure selective adherence of the lens in the mold. One surface of the pre-lens mold assembly can be selectively and rapidly heated to create a thermal gradient just prior to opening the mold assembly such that the heated mold half releases the lens while being opened, leaving the lens adhered to the other mold half. For example, U.S. Pat. No. 5,417,557 to Ross et al. teaches a laser assisted heating method to ensure selective adherence of a molded lens.

The first optical material of the present invention is a polymerizable or crosslinkable material that can be cured with heat or electromagnetic energy, e.g. light, to yield an optically clear and shape-sustaining polymer material. Particularly suitable optical materials include polymerizable or crosslinkable materials that are cured by actinic light, preferably UV light. Suitable materials for the first optical materials include hydrogel materials, rigid gas permeable materials and rigid materials that are known to be useful for producing contact lenses. Suitable hydrogel materials typically have a crosslinked hydrophilic network and hold between about 35% and about 75%, based on the total weight of the hydrogel material, of water. Examples of suitable hydrogel materials include copolymers having 2-hydroxyethyl methacrylate and one or more comonomers such as 2-hydroxy acrylate, ethyl acrylate, methyl methacrylate, vinyl pyrrolidone, N-vinyl acrylamide, hydroxypropyl methacrylate, isobutyl methacrylate, styrene, ethoxyethyl methacrylate, methoxy triethyleneglycol methacrylate, glycidyl methacrylate, diacetone acrylamide, vinyl acetate, acrylamide, hydroxytrimethylene acrylate, methoxy methyl methacrylate, acrylic acid, methacrylic acid, glyceryl ethacrylate and dimethylamino ethyl acrylate. Other suitable hydrogel materials include copolymers having methyl vinyl carbazole or dimethylamino ethyl methacrylate. Another group of suitable hydrogel materials include crosslinkable materials such as modified polyvinyl alcohols, for example, disclosed in U.S. Pat. No. 5,508,317, issued to Beat Müller. Suitable rigid gas permeable materials for the present invention include cross-linked siloxane polymers. The network of such polymers incorporates appropriate cross-linkers such as N,N'-dimethyl bisacrylamide, ethylene glycol diacrylate, trihydroxy propane triacrylate, pentaerythtritol tetraacrylate and other similar polyfunctional acrylates or methacrylates, or vinyl compounds, e.g., N-methylamino divinyl carbazole. Suitable rigid materials include acrylates (e.g., methacrylates), diacrylates and dimethacrylates, pyrolidones, styrenes, amides, acrylamides, carbonates, vinyls, acrylonitrieles, nitriles, sulfones and the like. Of the suitable materials, hydrogel materials are particularly suitable for the present invention. The polymerizable or crosslinkable materials of the present invention may contain a thermally acitvatable free radical initiator, e.g., azoisobutyronitile, benozyl peroxide, percarbonate or peracetate; or a photochemical initiator, e.g., substituted benzophenone, acetophenone, benzoin methyl ether, 1-hydroxycyclohexylphenyl ketone, and Darocur® and Irgacur® products, preferably Darocur® 1173 and Irgacur® 2959, by Ciba Specialty Chemical.

In accordance with the invention, preferred suitable materials for the first optical material are polymer-forming materials that are cured without or substantially without dimensional changes. Preferably, a suitable first optical material shrinks equal to or less about 5%, more preferably equal to or less than about 1%, by volume. Most preferably, a suitable first optical material is a non-shrinking material. Such substantially non-shrinking and non-shrinking materials include crosslinkable and polymerizable materials that cure in fully hydrated state. Exemplary non-shrinking polymers are disclosed in above-indicated U.S. Pat. No. 5,508, 317.

Although the pre-lens containing the first optical material is described above with a cast molded or double side molded article for illustration purposes, it is to be noted that the pre-lens can be produced by any known process, such as a spincasting or lathe forming process.

Once the pre-lens is formed, a second optical material is placed on one of the flat curves of the pre-lens. The second optical material can be a prefabricated insert or a curable liquid material that can be cured on the pre-lens. In accordance with the invention, the size of the second optical material (200) should be smaller than the size of the final multifunctional ophthalmic lens (400) to ensure that the second optical material is completely embedded in the first optical material.

As indicated above, the second optical material provides at least one optical function or property different from the first optical material, e.g., index of refraction, diffraction, polarization, or range of light absorption wavelength. The second optical material can be an optical material that is chemically different from the first optical material or the same optical material that has been modified to provide different optical properties. For example, a pigment, U.V. absorbing agent, or refraction-modifying agent can be blended or co-polymerized with the monomers or reactants that form the first optical material to modify the optical properties.

In selecting a suitable second optical material, various factors may be considered. Important factors include chemical compatibility of the first and second optical materials, shrinkage of the optical materials during the curing process, and swellability of the optical materials in various solvents and fluids. For example, when the two optical materials have substantially similar chemical structures and/or polarities, the adhesion between the two optical materials should be acceptable, and delamination of the two materials should not occur. If the two optical materials are significantly incompatible, a tie-layer or an optically acceptable glue can be used to ensure that the materials do not delaminate during normal use of the multifunctional lens. As another preferred embodiment of the invention, the second optical material can be modified to improve the adhesion between the first and second optical materials. For example, when a prefabricated insert (200) is used as the second optical material and the second optical material is not chemically compatible with the first optical material, the surface of the insert can be treated to compatibilize the interface between the two optical materials. Exemplary processes for compatibilizing the surface of the insert include plasma treatments, corona treatments and grafting treatments. Alternatively, an optically clear adhesive can be utilized to bond the second optical insert (200) to the first optical material (100, 300). Although the adhesion compatibility of the optical materials of the present multifunctional lens is discussed herein, the compatibility of the optical materials is not as critical as that of conventional composite lenses, which are merely laminated products of different optical layers, since the second optical material of the present multifunctional lens is completely encapsulated in the first optical material.

Suitable materials for the second optical material include polymerizable or crosslinkable materials that can be cured with heat or electromagnetic energy, e.g. light, to yield an optically clear and shape-sustaining polymer material. Suitable second optical materials can also be selected from the polymerizable and crosslinkable materials disclosed above with respect to the first optical material. Preferably, the second optical material is selected from a curable or polymeric material that is chemically compatible with the first optical material, and more preferably, the second optical material is the first optical material that has been modified to provide at least one different optical property. Employing one optical material for both first and second optical materials is advantageous in that the adhesion between the materials is assured and the dimensional changes of the materials created by exposures to different solvents and temperatures during normal use of the multifunctional lens do not cause delamination the materials and/or optical distortion of the lens.

After the second lens material is formed or placed on the pre-lens, the pre-lens is molded again in a finishing lens mold assembly to form the multifunctional ophthalmic lens. The finishing lens mold assembly has a male mold half and a female mold half. As for the finished curve embodiment of the present invention, the finishing lens mold assembly is formed by fitting a matching male or female lens mold half over the pre-lens mold half that contains the pre-lens and the second optical material. The closed finishing lens mold assembly has a lens cavity which is thicker or larger and thicker than the combined size of the pre-lens and the second optical material.

The multifunctional lens can be formed by, for example, placing the pre-lens having the second optical material in the female mold half of the finishing lens mold assembly with the second optical material exposed; placing a sufficient amount of the first optical material over the pre-lens and the second optical material to fill the lens cavity of the finishing mold assembly; closing the mold assembly with the male mold half of the mold assembly to define the shape of the final lens; and then curing the first optical material while applying pressure on the mold assembly to properly define the shape of the lens. Alternatively, the multifunctional lens can be formed by placing a sufficient amount of the first optical material in the female mold half of the finishing lens mold assembly; placing the pre-lens with the second optical material over the first optical material; placing the male mold half to close the mold assembly; and then curing the first optical material.

As for the finished curve embodiment of the invention, when the female pre-lens mold half is designed to retain the pre-lens, a sufficient amount of the fluid first optical material is placed over the second optical material and the pre-lens to fill the lens cavity, and the finishing lens assembly is closed. The optical material in the lens assembly is cured to produce the multifunctional ophthalmic lens. When the male pre-lens mold half is designed to retain the pre-lens, a sufficient amount of the first optical material is placed in a matching female mold half, the male pre-lens mold half is placed over the female mold half, and the optical material is cured.

Yet another embodiment of the present invention, when a relatively viscous first optical material is used, the insert molding process can be conducted in one curing step for the first optical material. The term "relatively viscous first optical material" as used herein indicates a curable optical material having a viscosity that does not allow or readily allow the second optical material from gravitationally settle or sink during the curing step. In this embodiment, the steps of the molding process include placing an amount of the curable first optical material in the female mold half of the finishing mold assembly, placing a second optical material over the first optical material, placing an additional amount of the curable first optical material over the second optical material, closing the finishing mold assembly with a matching male mold half, and then curing the optical materials in the closed finishing mold assembly to form the multifunctional composite lens. The second optical material in this embodiment can be a precured optical material or a curable material that can be cured simultaneously with the first optical material.

According the present invention, since the first optical material is polymerized or crosslinked over the chemically identical material, i.e., the previously cured first optical material of the pre-lens, the later applied first optical material strongly adheres to the first optical material of the pre-lens. Therefore, advantageously, the second optical material is stably embedded or affixed in the cured first optical material. In addition, the multifunctional lens of the present invention is highly advantageous in that the second optical material can be selected from a wide variety of optical materials, including biocompatible and non-biocompatible optical materials. Because the first optical material completely encapsulate the second optical material, the second material does not have to be biocompatible with the ocular environment. Furthermore, since the last step for producing the multifunctional lens of the present invention is a double-sided molding process, the molded multifunctional lens does not have to be further processed to form a finished lens. In contrast, conventional composite lens production processes require complicated and labor-intensive laminating and/or finish lathing or polishing step.

As indicated above, one or more of optical materials can be used to produce the multifunctional ophthalmic lens of the present invention. Of the above-indicated suitable optical materials, preferred optical materials include those which are described in U.S. Pat. No. 5,508,317, issued to Beat Müller on Apr. 16, 1996 and assigned to Ciba-Geigy Corporation. U.S. Pat. No. 5,508,317 in its entirety is incorporated herein by reference. A preferred group of optical materials, as described in U.S. Pat. No. 5,508,317, are those that comprise a 1,3-diol basic structure in which a certain percentage of the 1,3-diol units have been modified to a 1,3-dioxane having in the 2-position a radical that is polymerizable but not polymerized. These polymerizable materials are preferred in that the materials do not or substantially do not shrink while being cured. The polymerizable radical is especially an aminoalkyl radical having a polymerizable group bonded to the nitrogen atom. The optical material is preferably a derivative of a polyvinyl alcohol having a weight average molecular weight, $M_w$, of at least about 2,000 that, based on the number of hydroxy groups of the polyvinyl alcohol, comprises from approximately 0.5 to approximately 80% of units of formula I:

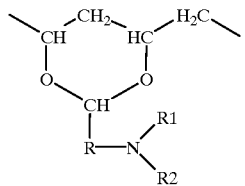

(I)

wherein:
R is lower alkylene having up to 8 carbon atoms,
$R^1$ is hydrogen or lower alkyl and
$R^2$ is an olefinically unsaturated, electron-attracting, copolymerizable radical preferably having up to 25 carbon atoms. $R^2$ is, for example, an olefinically unsaturated acyl radical of formula $R^3$—CO—, in which
$R^3$ is an olefinically unsaturated copolymerizable radical having from 2 to 24 carbon atoms, preferably from 2 to 8 carbon atoms, especially preferably from 2 to 4 carbon atoms.

In another embodiment, the radical $R^2$ is a radical of formula II

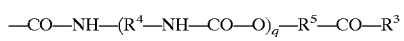

wherein
q is zero or one and
$R^4$ and $R^5$ are each independently lower alkylene having from 2 to 8 carbon atoms, arylene having from 6 to 12 carbon atoms, a saturated divalent cycloaliphatic group having from 6 to 10 carbon atoms, arylenealkylene or alkylenearylene having from 7 to 14 carbon atoms or arylenealkylenearylene having from 13 to 16 carbon atoms, and
$R^3$ is as defined above.

Lower alkylene R preferably has up to 8 carbon atoms and may be straight-chained or branched. Suitable examples include octylene, hexylene, pentylene, butylene, propylene, ethylene, methylene, 2-propylene, 2-butylene and 3-pentylene. Preferably lower alkylene R has up to 6 and especially preferably up to 4 carbon atoms. The meanings methylene and butylene are especially preferred. $R^1$ is preferably hydrogen or lower alkyl having up to seven, especially up to four, carbon atoms, especially hydrogen.

As for $R^4$ and $R^5$, lower alkylene $R^4$ or $R^5$ preferably has from 2 to 6 carbon atoms and is especially straight-chained. Suitable examples include propylene, butylene, hexylene, dimethylethylene and, especially preferably, ethylene. Arylene $R^4$ or $R^5$ is preferably phenylene that is unsubstituted or is substituted by lower alkyl or lower alkoxy, especially 1,3-phenylene or 1,4-phenylene or methyl-1,4-phenylene. A saturated divalent cycloaliphatic group $R^4$ or $R^5$ is preferably cyclohexylene or cyclohexylene-lower alkylene, for example cyclohexylenemethylene, that is unsubstituted or is substituted by one or more methyl groups, such as, for example, trimethylcyclohexylenemethylene, for example the divalent isophorone radical. The arylene unit of alkylenearylene or arylenealkylene $R^4$ or $R^5$ is preferably phenylene, unsubstituted or substituted by lower alkyl or lower alkoxy, and the alkylene unit thereof is preferably lower alkylene, such as methylene or ethylene, especially methylene. Such radicals $R^4$ or $R^5$ are therefore preferably phenylenemethylene or methylenephenylene. Arylenealkylenearylene $R^4$ or $R^5$ is preferably phenylene-lower alkylene-phenylene having up to 4 carbon atoms in the alkylene unit, for example phenyleneethylenephenylene. The radicals $R^4$ and $R^5$ are each independently preferably lower alkylene having from 2 to 6 carbon atoms, phenylene, unsubstituted or substituted by lower alkyl, cyclohexylene or cyclohexylene-lower alkylene, unsubstituted or substituted by lower alkyl, phenylene-lower alkylene, lower alkylene-phenylene or phenylene-lower alkylene-phenylene.

Within the scope of this invention, the term "lower" used in connection with radicals and compounds denotes radicals or compounds having up to 7 carbon atoms, preferably up to 4 carbon atoms, unless defined otherwise. Lower alkyl has especially up to 7 carbon atoms, preferably up to 4 carbon atoms, and is, for example, methyl, ethyl, propyl, butyl or tert-butyl. Lower alkoxy has especially up to 7 carbon atoms, preferably up to 4 carbon atoms, and is, for example, methoxy, ethoxy, propoxy, butoxy or tert-butoxy.

The olefinically unsaturated copolymerizable radical $R^3$ having from 2 to 24 carbon atoms is preferably alkenyl having from 2 to 24 carbon atoms, especially alkenyl having from 2 to 8 carbon atoms and especially preferably alkenyl having from 2 to 4 carbon atoms, for example ethenyl, 2-propenyl, 3-propenyl, 2-butenyl, hexenyl, octenyl or dodecenyl. The meanings ethenyl and 2-propenyl are preferred, so that the group —CO—$R^3$ is the acyl radical of acrylic or methacrylic acid.

The divalent group —$R^4$—NH—CO—O— is present when q is one and absent when q is zero. Prepolymers in which q is zero are preferred.

The divalent group —CO—NH—$R^4$—NH—CO—O)$_q$—$R^5$—O— is present when p is one and absent when p is zero.

Prepolymers in which p is zero are preferred. In prepolymers in which, p is one the index q is preferably zero. Prepolymers in which p is one, the index q is zero and $R^5$ is lower alkylene are especially preferred.

A preferred prepolymer optical material is a derivative of a polyvinyl alcohol having a molecular weight of at least about 2000 that, based on the number of hydroxy groups of the polyvinyl alcohol, comprises from approximately 0.5 to approximately 80% of units of formula III in which R is lower alkylene having up to 6 carbon atoms, p is zero and $R^3$ is alkenyl having from 2 to 8 carbon atoms.

A more preferred prepolymer optical material is a derivative of a polyvinyl alcohol having a molecular weight of at least about 2000 that, based on the number of hydroxy groups of the polyvinyl alcohol, comprises from approximately 0.5 to approximately 80% of units of formula III in which R is lower alkylene having up to 6 carbon atoms, p is one, q is zero, $R^5$ is lower alkylene having from 2 to 6 carbon atoms and $R^3$ is alkenyl having from 2 to 8 carbon atoms.

Yet a more preferred prepolymer optical material is a derivative of a polyvinyl alcohol having a molecular weight of at least about 2000 that, based on the number of hydroxy groups of the polyvinyl alcohol, comprises from approximately 0.5 to approximately 80% of units of formula III in which R is lower alkylene having up to 6 carbon atoms, p is one, q is one, R4 is lower alkylene having from 2 to 6 carbon atoms, phenylene, unsubstituted or substituted by lower alkyl, cyclohexylene or cyclohexylene-lower alkylene, unsubstituted or substituted by lower alkyl, phenylene-lower alkylene, lower alkylene-phenylene or phenylene-lower alkylene-phenylene, $R^5$ is lower alkylene having from 2 to 6 carbon atoms and $R^3$ is alkenyl having from 2 to 8 carbon atoms.

Polyvinyl alcohols that can be derivatised in accordance with the invention preferably have a molecular weight of at least 10,000. As an upper limit the polyvinyl alcohols may have a molecular weight of up to 1,000,000. Preferably, the polyvinyl alcohols have a molecular weight of up to 300,000, especially up to approximately 100,000 and especially preferably up to approximately 50,000.

Polyvinyl alcohols suitable in accordance with the invention usually have a poly(2-hydroxy)ethylene structure. The polyvinyl alcohols derivatised in accordance with the invention may, however, also comprise hydroxy groups in the form of 1,2-glycols, such as copolymer units of 1,2-dihydroxyethylene, as may be obtained, for example, by the alkaline hydrolysis of vinyl acetate/vinylene carbonate copolymers.

In addition, the polyvinyl alcohols derivatised in accordance with the invention may also comprise small proportions, for example up to 20%, preferably up to 5%, of copolymer units of ethylene, propylene, acrylamide, methacrylamide, dimethacrylamide, hydroxyethyl methacrylate, methyl methacrylate, methyl acrylate, ethyl acrylate, vinylpyrrolidone, hydroxyethyl acrylate, allyl alcohol, styrene or similar customarily used comonomers.

Commercially available polyvinyl alcohols may be used, such as, for example, Vinol® 107 produced by Air Products (MW=22,000 to 31,000, 98–98.8% hydrolysed), Polysciences 4397 (MW=25,000, 98.5% hydrolysed), BF 14 produced by Chan Chun, Elvanol® 90-50 produced by DuPont, UF-120 produced by Unitika, Moviol® 4-88, 10-98 and 20-98 produced by Hoechst. Other manufacturers are, for example, Nippon Gohsei (Gohsenol®), Monsanto (Gelvatol®), Wacker (Polyviol®) and the Japanese manufacturers Kuraray, Denki and Shin-Etsu. The molecular weights referenced herein are weight average weights, Mw, determined by gel permeation chromatography, unless otherwise specified.

It is also possible to use copolymers of hydrolysed vinyl acetate, which are obtainable, for example, in the form of hydrolysed ethylene/vinyl acetate (EVA), or vinyl chloride/vinyl acetate, N-vinylpyrrolidone/vinyl acetate and maleic acid anhydride/vinyl acetate. In a preferred embodiment, the polyvinyl alcohol derivatised in accordance with the invention comprises less than 50% of polyvinyl acetate units, especially less than 20% of polyvinyl acetate units. Preferred amounts of residual acetate units in the polyvinyl alcohol derivatised in accordance with the invention, based on the sum of vinyl alcohol units and acetate units, are approximately from 3 to 20%, preferably approximately from 5 to 16% and especially approximately from 10 to 14%.

The compounds comprising units of formula III may be prepared in a known manner. For example, a polyvinyl alcohol having a molecular weight of at least about 2000 that comprises unit of formula IV

may be reacted with approximately from 0.5 to 80%, based on the number of hydroxy groups of the compound of formula IV, of a compound of formula (V)

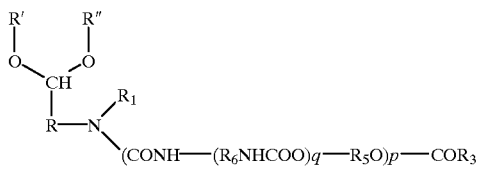

in which R' and R are each independently hydrogen, lower alkyl or lower alkanoyl, such as acetyl or propionyl, and the other variables are as defined for formula III, especially in an acidic medium.

Alternatively, a polyvinyl alcohol having a molecular weight of at least about 2000 that comprises units of formula IV may be reacted with a compound of formula VI:

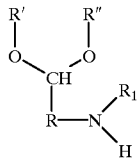

in which the variables are as defined for the compound of formula V, especially under acidic conditions, and the cyclic acetal obtainable in that manner may then be reacted with a compound of formula VII

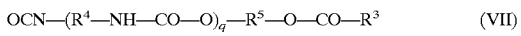

in which the variables are as defined for the compound of formula V.

Alternatively, the product obtainable as described above from a compound of formula IV and a compound of formula VI may be reacted with a compound of formula (VIII)

in which $R^3$ is, for example, alkenyl having from 2 to 8 carbon atoms and X is a reactive group, for example, etherified or esterified hydroxy, or halogen, e.g., chlorine.

Compounds of formula V in which p is zero are known, for example, from EP 201 693. Compounds of formula VI are also described therein. Compounds of formula VII are also known and can be prepared in a known manner. An example of a compound of formula VII in which q is zero is isocyanatoethyl methacrylate. An example of a compound of formula VII in which q is one is the reaction product of isophorone diisocyanate with 0.5 equivalent of hydroxyethyl methacrylate. Compounds of formula VIII are known, and methacryloyl chloride is an exemplary compound thereof. Compounds of formula V in which p and/or q are 1 can be prepared in a known manner from the above-mentioned compounds, for example by reaction of a compound of formula VI with isocyanatoethyl methacrylate or by reaction of a compound of formula VI with isophorone diisocyanate which has previously been terminated with 0.5 equivalent of hydroxyethyl methacrylate.

The prepolymer optical materials of formulae I and III are crosslinkable in an extremely effective and controlled manner, especially by photocrosslinking. Molded ophthalmic lenses may also be obtained by photocrosslinking a prepolymer optical material comprising units of formula I or III with or without an additional vinylic comonomer, which is water-insoluble.

In the case of photocrosslinking, it is appropriate to add a photoinitiator which can initiate radical crosslinking. Examples thereof are familiar to the person skilled in the art and suitable photoinitiators that may be mentioned specifically are benzoin methyl ether, 1-hydroxycyclohexylphenyl ketone, Darocur® 1173 or Irgacure types. The crosslinking can then be triggered by actinic radiation, such as, for example, UV light, or ionising radiation, such as, for example, gamma radiation or X-radiation.

The photopolymerization is may occur in the presence of a solvent. A suitable solvent is in principle any solvent that dissolves polyvinyl alcohol and the vinylic comonomers optionally used in addition, for example water, alcohols, such as lower alkanols, for example ethanol or methanol, also carboxylic acid amides, such as dimethylformamnide, or dimethyl sulfoxide, and also a mixture of suitable solvents, such as, for example, a mixture of water with an alcohol, such as, for example, a water/ethanol or a water/methanol mixture.

The photocrosslinking is carried out preferably directly from an aqueous solution of the preferred prepolymers, which can be obtained by the preferred purification step, ultrafiltration, where appropriate after the addition of an additional vinylic comonomer. For example, an approximately 15 to 40% aqueous solution can be photocrosslinked.

The process for the preparation of the polymers of the invention may comprise, for example, photocrosslinking a prepolymer comprising units of formula I or III, especially in substantially pure form, for example, after single or repeated ultrafiltration, preferably in solution, especially in aqueous solution, in the absence or presence of an additional vinylic comonomer.

The vinylic comonomer which, in accordance with the invention, may be used in addition in the photocrosslinking, may be hydrophilic or hydrophobic, or a mixture of a hydrophobic and a hydrophilic vinylic monomer. Suitable vinylic monomers include especially those customarily used in the manufacture of contact lenses. A hydrophilic vinylic monomer denotes a monomer that typically yields as homopolymer a polymer that is water-soluble or can absorb at least 10% by weight of water. Analogously, a hydrophobic vinylic monomer denote, a monomer that typically yields as homopolymer a polymer that is water-insoluble and can absorb less than 10% by weight of water. Generally, approximately from 0.01 to 80 units of a typical vinylic comonomer is reacted per unit of formula I or III.

Suitable hydrophobic vinylic comonomers include, without the list being exhaustive, $C_1$–$C_{18}$ alkyl acrylates and methacrylates, $C_3$–$C_{18}$alkyl acrylamides and methacrylamides, acrylonitrile, methacrylonitrile, vinyl-$C_1$–$C_{18}$alkanoates, $C_2$–$C_{18}$alkenes, $C_2$–$C_{18}$haloalkenes, styrene, $C_1$–$C_6$alkylstyrene, vinyl alkyl ethers, in which the alkyl moiety contains from 1 to 6 carbon atoms, $C_2$–$C_{10}$perfluoroalkyl acrylates and methacrylates or correspondingly partially fluorinated acrylates and methacrylates, $C_3$–$C_{12}$perfluoroalkyl-ethylthiocarbonylaminoethyl acrylates and methacrylates, acryloxy- and methacryloxy-alkylsiloxanes, N-vinylcarbazole, $C_1C_{12}$alkyl esters of maleic acid, fumaric acid, itaconic acid, mesaconic acid and the like. $C_1$–$C_4$alkyl esters of vinylically unsaturated carboxylic acids having from 3 to 5 carbon atoms or vinyl esters of carboxylic acids having up to 5 carbon atoms, for example, are preferred.

Examples of suitable hydrophobic vinylic comonomers include methyl acrylate, ethyl acrylate, propyl acrylate, isopropyl acrylate, cyclohexyl acrylate, 2-ethylhexyl acrylate, methyl methacrylate, ethyl methacrylate, propyl methacrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyltoluene, vinyl ethyl ether, perfluorohexylethylthiocarbonylaminoethyl methacrylate, isobomyl methacrylate, trifluoroethyl methacrylate, hexafluoroisopropyl methacrylate, hexafluorobutyl methacrylate, tris-trimethylsilyloxy-silyl-propyl methacrylate, 3-methacryloxypropyl-pentamethyldisiloxane and bis(methacryloxypropyl)tetramethyldisiloxane.

Suitable hydrophilic vinylic comonomers include, without the list being exhaustive, hydroxy-substituted lower alkyl acrylates and methacrylates, acrylamide, methacrylamide, lower alkyl acrylamides and methacrylamides, ethoxylated acrylates and methacrylates, hydroxy-substituted lower alkyl acrylamides and methacrylamides, hydroxy-substituted lower alkyl vinyl ethers, sodium ethylenesulfonate, sodium styrenesulfonate, 2-acrylamido-2-methylpropanesulfonic acid, N-vinylpyrrole, N-vinylsuccinimide, N-vinylpyrrolidone, 2- or 4-vinylpyridine, acrylic acid, methacrylic acid, amino-(the term "amino" also including quaternary ammonium), mono-lower alkylamino- or di-lower alkylamino-lower alkyl acrylates and methacrylates, allyl alcohol and the like. Hydroxy-substituted $C_2$–$C_4$alkyl(meth)acrylates, five- to seven-membered N-vinyl lactams, N,N-di-$C_1$–$C_4$alkyl (meth)acrylamides and vinylically unsaturated carboxylic acids having a total of from 3 to 5 carbon atoms, for example, are preferred.

Examples of suitable hydrophilic vinylic comonomers include hydroxyethyl methacrylate, hydroxyethyl acrylate, acrylamide, methacrylamide, dimethylacrylamide, allyl alcohol, vinylpyridine, vinylpyrrolidone, glycerol methacrylate, N-(1,1-dimethyl-3-oxobutyl)acrylamide, and the like. Preferred hydrophobic vinylic comonomers are methyl methacrylate and vinyl acetate, and preferred hydrophilic vinylic comonomers are 2-hydroxyethyl methacrylate, N-vinylpyrrolidone and acrylamide.

The multifunctional ophthalmic lens of the present invention can be designed to provide a wide range of different optical and ophthalmic functions. In addition, the final step for producing the present multifunctional ophthalmic lens is a molding process. Consequently, the present lens production process does not require time-consuming and labor-intensive cutting and finishing steps of conventional composite lens production processes, e.g., lathe forming processes. Moreover, the present molding process for producing multifunctional lenses provides a simplified production method that is highly suitable for a large-scale production of multifunctional lenses.

The present invention is further illustrated with the following examples. However, the examples are not to be construed as limiting the invention thereto.

EXAMPLES

Example 1

A polypropylene pre-lens male and female mold halves are injection molded. The mold halves are designed to produce a pre-lens having a diameter of about 14.5 mm, a thickness of about 0.1 mm and a sagittal depth of about 4.0 mm. The male mold half has an indentation that creates a round pocket, which has a 8 mm diameter and a 0.05 mm depth, in the optical zone of the molded pre-lens. The female mold half is oxygen plasma treated to ensure that the pre-lens adheres to the female mold half when the pre-lens is formed and the pre-lens mold is opened. The plasma treatment is conducted in a plasma fixture of the type described in Ultrathin coating of plasma polymer of methane applied on the surface of silicone contact lenses, C. P. Ho and H. Yasuda, Journal of Biomedical Materials Research, Vol. 22, 919–937 (1988). A vacuum of about 0.3 torr is applied and the oxygen flow rate of about 3 $cm^3$/min is used. The plasma was generated using a radio frequency power of about 100 watts, and the lens mold half is treated for about 4 minutes. About 0.06 ml of the nelfilcon lens monomer composition is deposited on the center portion of the female mold half, and the matching male pre-lens mold half is placed over the female mold half, forming a pre-lens mold assembly. Briefly, nelfilcon is a product of a crosslinkable modified polyvinyl alcohol which contains about 0.48 mmol/g of an acryamide crosslinker. The polyvinyl alcohol has about 7.5 mol % acetate content. Nelfilcon has a solid content of about 30% and contains about 0.1% of a photoinitiator, Durocure® 1173. The monomer composition is cured by exposing the pre-lens assembly for about 15 seconds under a U.V. radiation of about 2.5 mW/$cm^2$. The mold assembly is then opened leaving the pre-lens adhere to the female mold half.

A second optical material having a diameter of about 7.8 mm, a thickness of about 0.05 mm and a sagittal depth of about 1 mm is separately produced using a conventional double sided molding process. The second optical material is a tinted lens and is produced by adding about 2.5 w/w % of copper thalocyanide to the above-described nelfilcon composition.

The second optical material is placed in the pocket of the pre-lens. Then about 0.06 ml of the nelfilcon composition is placed over the pocket, covering the second optical material and the pre-lens. A polypropylene matching male finishing mold half is mated with the female pre-lens mold half, which contains the pre-lens and the second optical material, to form the final lens mold assembly. The finishing male mold half has a dimension such that the mated finishing lens mold assembly form a lens cavity which has a diameter of about 14.5 mm and a center thickness of about 0.23 mm. The finishing lens mold assembly is then exposed to an about 2.5 mW/$cm^2$ U.V. radiation for about 15 seconds to produce a fully cured composite lens. The lens mold is opened and the composite lens is removed.

The composite lens has a tinted optical zone, and the tinted second optical material in the composite lens is completely and cohesively embedded in the outside nelfilcon material.

Example 2

The procedure outlined in Example 1 is repeated, except a diffractive grating material is used as the second optical material. The diffractive grating material is a copolymer of phenylethyl acrylate and phenylethyl methacrylate and is further described in U.S. Pat. No. 5,433,746 to F. Namdaran et al. The produced composite lens exhibits two optical powers. One optical power is exhibited by the combination of the two optical materials in the region where the two optical materials overlap, and another optical power is exhibited by the nelfilcon material in the region outside the embedded second optical material.

Example 3

The procedure outlined in Example 1 is repeated, except a birefingent material is used as the second optical material. The birefringent material is produced from a polyethylene terephthalate (PET) sheet. The PET sheet is heated to about 90° C. and is uniaxially stretched to a draw ratio of about 4.5:1. The uniaxially oriented PET sheet is cooled and then shaped using a conventional contact lens lathing machine.

The resulting composite lens is a bifocal contact lens that provides two optical powers. The two optical powers is mainly provided by the differing indices of refraction of the second optical material.

Example 4

A molded composite ophthalmic lens is produced using tefilcon and atlafilcon. The tefilcon composition is modified in this example by adding about 40 w/w % of water to the tefilcon composition. The modified tefilcon material does not shrink during the polymerization process. Briefly, the modified tefilcon contains about 59.3% of hydroxy ethyl methacrylate, about 0.2% of benzoin methyl ether, about 40% of water and about 0.5% of ethylene glycol dimethacrylate. Atlafilcon contains about 85% dimethyl sulfoxide, about 10% polyvinyl alcohol, about 4% methyl methacrylate, about 1% isocyanatoethyl methacrylate and small amounts of benzoin methyl ether and sodium acetate.

A lens mold having the dimension disclosed in Example 1 for the finishing lens mold assembly is used to produce the composite lens. About 0.45 g of the modified tefilcon material is placed in the female mold half. A separately produced second optical material is placed on the tefilcon material. The second optical material is produced from the Atlafilcon material using a conventional double sided molding process. On top of the second optical material, about 0.45 g of the modified tefilcon material is placed. The female mold is the closed with a matching male mold to form a finishing lens mold assembly. The mold assembly is cured under a U.V. radiation of about 2.5 mW/$cm^2$ for 30 minutes, and then heat treated for 60 minutes at 118° C. The heat treated mold assembly is cooled, and the composite lens is removed from the mold.

The composite lens clearly demonstrates the concept that a molded composite lens can be produced from two different optical materials.

What is claimed is:

1. A cast molded multifunctional ophthalmic lens comprising a first optical component and a second optical component wherein said first optical component encapsulates said second optical component such that said first optical component provides a first optical function and said second optical component provides a second optical function, wherein said first optical component is produced from a composition which comprises a curable fluid material that does not significantly shrink while being cured.

2. The molded ophthalmic lens of claim 1 wherein said curable fluid material shrinks equal to or less than about 5 volume % while being cured.

3. The molded ophthalmic lens of claim 2 wherein said second optical function includes a diffraction, reflection, light filtration, light polarization, or cosmetic function.

4. The molded ophthalmic lens of claim 3 wherein said first optical material is a hydrogel, rigid gas permeable, or rigid optical material, and said second optical material is another hydrogel, rigid gas permeable, or rigid optical material.

5. The molded ophthalmic lens of claim 4 wherein said first and second optical materials comprise a derivative of polyvinyl alcohol comprising units of formula I:

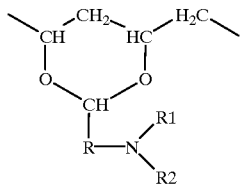
(I)

wherein:

R is lower alkylene having up to 8 carbon atoms, $R^1$ is hydrogen or lower alkyl, and $R^2$ is an olefinically unsaturated, electron-attracting, copolymerizable radical preferably having up to 25 carbon atoms.

6. A cast molded composite ophthalmic lens comprising an outer layer optical component and an inner layer optical component having a different optical property wherein said outer optical component encapsulates said inner optical component such that said inner optical component is firmly affixed in said outer optical component, wherein said outer optical component is produced from a composition which comprises a curable fluid material that does not significantly shrink while being cured.

7. The molded ophthalmic lens of claim 6 wherein said inner optical component provides a different optical function than said outer optical component, and said different optical function includes a diffraction, reflection, light filtration, light polarization, or cosmetic function.

8. The molded ophthalmic lens of claim 7 wherein said outer optical material is a hydrogel, rigid gas permeable, or rigid optical material, and said inner optical material is another hydrogel, rigid gas permeable, or rigid optical material.

9. The molded ophthalmic lens of claim 8 wherein said inner and outer optical materials comprise a derivative of polyvinyl alcohol comprising units of formula I:

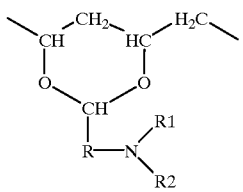
(I)

wherein:

R is lower alkylene having up to 8 carbon atoms, $R^1$ is hydrogen or lower alkyl, and $R^2$ is an olefinically unsaturated, electron-attracting, copolymerizable radical preferably having up to 25 carbon atoms.

10. The molded ophthalmic lens of claim 6 wherein said curable fluid material shrinks equal to or less than about 5 volume % while being cured.

* * * * *